US012791372B2

(12) United States Patent
Matanic

(10) Patent No.: US 12,791,372 B2
(45) Date of Patent: Nov. 10, 2026

(54) DEVICE FOR PORTIONED DISPENSING OF A LIQUID MEDIUM

(71) Applicant: NOVAPACIS UG (HAFTUNGSBESCHRÄNKT), Monheim am Rhein (DE)

(72) Inventor: Frank Matanic, Düsseldorf (DE)

(73) Assignee: NOVAPACIS UG, Monheim am Rhein (DE)

( * ) Notice: Subject to any disclaimer, the term of this patent is extended or adjusted under 35 U.S.C. 154(b) by 56 days.

(21) Appl. No.: 18/848,800

(22) PCT Filed: Mar. 22, 2023

(86) PCT No.: PCT/EP2023/057375
§ 371 (c)(1),
(2) Date: Sep. 19, 2024

(87) PCT Pub. No.: WO2023/180401
PCT Pub. Date: Sep. 28, 2023

(65) Prior Publication Data

US 2025/0216237 A1 Jul. 3, 2025

(30) Foreign Application Priority Data

Mar. 22, 2022 (DE) ..................... 10 2022 000 980.3

(51) Int. Cl.
*G01F 11/02* (2006.01)
*A61F 9/00* (2006.01)
*A61M 31/00* (2006.01)

(52) U.S. Cl.
CPC .......... *G01F 11/028* (2013.01); *A61F 9/0008* (2013.01); *A61M 31/00* (2013.01); *A61M 2210/0618* (2013.01)

(58) Field of Classification Search
CPC ............... B05B 11/107; B05B 11/1074; B05B 11/1001; B05B 11/1004; G01F 11/028
(Continued)

(56) References Cited

U.S. PATENT DOCUMENTS 1,611,601 A * 12/1926 Mccall .................. G01F 11/028
222/321.5
2,128,567 A * 8/1938 Cahoon ............... B05B 11/1001
222/321.6

(Continued)

FOREIGN PATENT DOCUMENTS

AU 2008209125 B2 5/2013
DE 10151781 A1 5/2003

(Continued)

OTHER PUBLICATIONS

International Search Report for Application No. PCT/EP2023/057375, dated Jul. 18, 2023, 2 pages, English translation.

(Continued)

*Primary Examiner* — Charles P. Cheyney
(74) *Attorney, Agent, or Firm* — CANTOR COLBURN LLP

(57) ABSTRACT

A device for the portioned dispensing of a liquid medium includes

- two housing parts, which are arranged to be longitudinally movable relative to one another on a common longitudinal axis between an unactuated rest position and an actuated end position,
- a piston arranged axially fixed relative to the first part.
- a plunger arranged axially fixed relative to the second housing part and having a closed end face and a plunger casing,
- a dosing cavity enclosed by a piston inner wall, into which the plunger is lowered by actuation of the device, (Continued)

a liquid channel extending from the dosing cavity and in fluid communication with a valve-controlled discharge opening in the first part.

The device includes an inner sealing section formed on the piston inner wall, against which an outer sealing section formed on the outside of the plunger casing rests without a gap when the plunger is lowered into the dosing cavity.

10 Claims, 5 Drawing Sheets

(58) Field of Classification Search
USPC ............... 222/321.5–321.6, 321.7–321.9, 71
See application file for complete search history.

(56) References Cited

U.S. PATENT DOCUMENTS

| | | | | |
|---|---|---|---|---|
| 4,286,736 | A | 9/1981 | Corsette | |
| 4,685,594 | A * | 8/1987 | Czech | B05B 11/107 222/257 |
| 4,728,008 | A * | 3/1988 | Graf | B05B 15/30 222/321.5 |
| 4,921,142 | A * | 5/1990 | Graf | B05B 11/02 222/320 |
| 5,110,052 | A * | 5/1992 | Graf | B05B 11/1023 239/333 |
| 6,070,763 | A | 6/2000 | Gueret | |
| 8,348,096 | B2 | 1/2013 | Greiner-Perth | |
| 2002/0047027 | A1 * | 4/2002 | Sogaro | B05B 11/1001 222/321.9 |
| 2003/0121940 | A1 * | 7/2003 | Ichikawa | B05B 11/1074 222/321.9 |
| 2005/0006412 | A1 * | 1/2005 | Albisetti | B05B 11/1059 222/321.9 |
| 2006/0065675 | A1 * | 3/2006 | Bougamont | B05B 11/1026 222/321.9 |
| 2008/0115845 | A1 * | 5/2008 | Leuliet | B05B 11/1004 251/321 |
| 2010/0224653 | A1 * | 9/2010 | Donnette | B05B 11/1025 222/321.9 |
| 2010/0252581 | A1 * | 10/2010 | Greiner-Perth | B05B 11/107 222/320 |
| 2011/0073679 | A1 | 3/2011 | Greiner-Perth | |

FOREIGN PATENT DOCUMENTS

| | | | |
|---|---|---|---|
| DE | 102009017459 | A1 | 10/2010 |
| EP | 1194246 | A1 | 4/2002 |
| EP | 2939750 | A1 | 11/2015 |
| EP | 3072597 | B1 | 4/2020 |
| GB | 2140509 | A | 11/1984 |
| WO | 2016174031 | A1 | 11/2016 |

OTHER PUBLICATIONS

Written Opinion for Application No. PCT/EP2023/057375, dated Jul. 18, 2023, 3 pages, English translation.

* cited by examiner

DEVICE FOR PORTIONED DISPENSING OF A LIQUID MEDIUM

CROSS-REFERENCE TO RELATED APPLICATIONS

This application is a 35 U.S.C. § 371 National Stage patent application of PCT/EP2023/057375 filed 22 Mar. 2023, which claims the benefit of German patent application 10 2022 000 980.3 filed 22 Mar. 2022, the disclosures of which are incorporated herein by reference in their entirety.

TECHNICAL FIELD

The disclosure relates to a device for the portioned dispensing of a liquid, preferably therapeutic, medium according to the preamble of the claims.

BACKGROUND

Dosing devices for fluids, such as those known from EP 3 072 597 A1, have a dosing housing projecting into a fluid container, in which a piston is guided in a sealing manner. A pressure chamber is formed in the dosing housing. A valve acting opposite the fluid container is designed to close in the event of overpressure and to open in the event of underpressure. The geometry of the pressure chamber defines the dispensing volume per stroke. The piston is provided with an axial piston bore and is held in the rest position by a return spring. When the piston is actuated and moved axially, the fluid in the pressure chamber is first compressed and an overpressure is generated, thereby closing the valve. As soon as the valve is closed, the fluid is conveyed out through the piston bore when the piston continues to move axially and the valve is closed.

Conventional dosing devices often have to be actuated several times at the beginning in order to first displace air from the dosing housing by pumping several times before fluid is then drawn in from the stored supply. A correctly portioned dispensing quantity is therefore only achieved after repeated actuation. In addition, some systems are subject to a loss of discharge quantity after a longer period of non-use, when fluid in the dosing housing escapes due to gravity and returns to the reservoir.

The loss of dosing, combined with repeated strokes of the dosing device, is not a problem for applications in some technical areas. For medical products and pharmaceuticals, however, they are a decisive factor or disadvantage. For example, in the pharmaceutical development of a nasal spray pump, a rapid response must be tested in addition to the dosing accuracy per stroke, and appropriate instructions must also be available on the products.

A device for portioned dispensing of the generic type is known from DE 10 2009 017 459 A1. Other dispensing devices are known from DE 101 51 781 A1, EP 1 194 246 A1 or EP 2 939 750 A1, WO 2016/174031 A1 discloses a flexible dispensing housing that contracts when the fluid is actuated and dispensed.

SUMMARY

The disclosure is based on achieving a delay-free response when the device is actuated, with immediate discharge of the dosed discharge quantity, with low-cost manufacturability and a small number of components.

To solve this, a device for the portioned dispensing of a liquid medium with the features stated in the claims is proposed. The device comprises

- first and second housing parts which are arranged to be longitudinally movable relative to one another on a common longitudinal axis between an unactuated rest position and an actuated end position,
- a piston arranged axially fixed relative to the first housing part,
- a plunger arranged axially fixed relative to the second housing part, which is arranged in longitudinal alignment with the piston and is composed of a closed end face and a plunger casing,
- a dosing cavity which is enclosed by an inner wall of the piston and into which the plunger can be lowered by actuation of the device,
- a liquid channel which extends from the dosing cavity and is in fluid connection with a valve-controlled discharge opening in the first housing part.

The device according to the disclosure is characterized by an inner sealing section formed on the inner wall of the plunger, against which an outer sealing section formed on the outside of the plunger casing rests without a gap when the plunger is partially and fully lowered into the dosing cavity.

The actuation of the device can be divided into individual phases. The first phase is the still unactuated idle or initial state. In this state, there is no contact and therefore no mutual sealing between the piston and the plunger. Therefore, the therapeutic liquid, for example, can flow unhindered into the dosing cavity and fill it.

In the second and third phases, however, namely when the plunger is partially lowered into the dosing cavity and when the plunger is fully lowered, the inner sealing section lies against the opposite outer sealing section without a gap, so that the dosing cavity is separated from the liquid supply in the surrounding storage space from the second phase onwards. In the third phase, pressure is then applied to the separated medium, forcing it towards the discharge opening and out of it.

Advantageous, but not obligatory, designs of the device according to the disclosure are given in the individual subclaims.

In a first design, it is provided that the liquid channel is located in the piston, in that the liquid channel, starting from the base of the dosing cavity, initially runs along the piston, The storage space that stores the medium is preferably part of the second housing part. The valve-controlled discharge opening is preferably located on the first housing part.

It is advantageous for the function of the dosing cavity if the arrangement of inner and outer sealing section is located in the storage space and is surrounded by the storage space.

It is also advantageous for the function of the dosing cavity if the plunger is arranged on a plunger carrier facing away from the end face, wherein the plunger carrier is located in the storage space and is provided with a plurality of openings through which the medium can flow. The openings can be distributed around the circumference of the plunger carrier. In this case, the plunger carrier forms a movement space for the axially movable piston arranged therein.

The inner wall of the dosing cavity can be designed as a circular cylindrical longitudinal section over the majority of its length, which is adjoined by a conically tapering longitudinal section towards the plunger.

A valve arranged in the transition between the dosing cavity and the liquid channel is also proposed. The valve is designed to open only towards the liquid channel. In a displacement phase, the valve enables compression in the dosing cavity. Only when a discharge phase is reached does the valve open and release the liquid channel for the medium to flow through, wherein the valve prevents leakage, backflow or contamination of the medium stored in the storage space once the discharge has been completed.

BRIEF DESCRIPTION OF THE DRAWINGS

Exemplary embodiments of the device are explained below in further detail and with reference to the drawings, wherein.

DETAILED DESCRIPTION OF THE DRAWINGS

Figure 1:
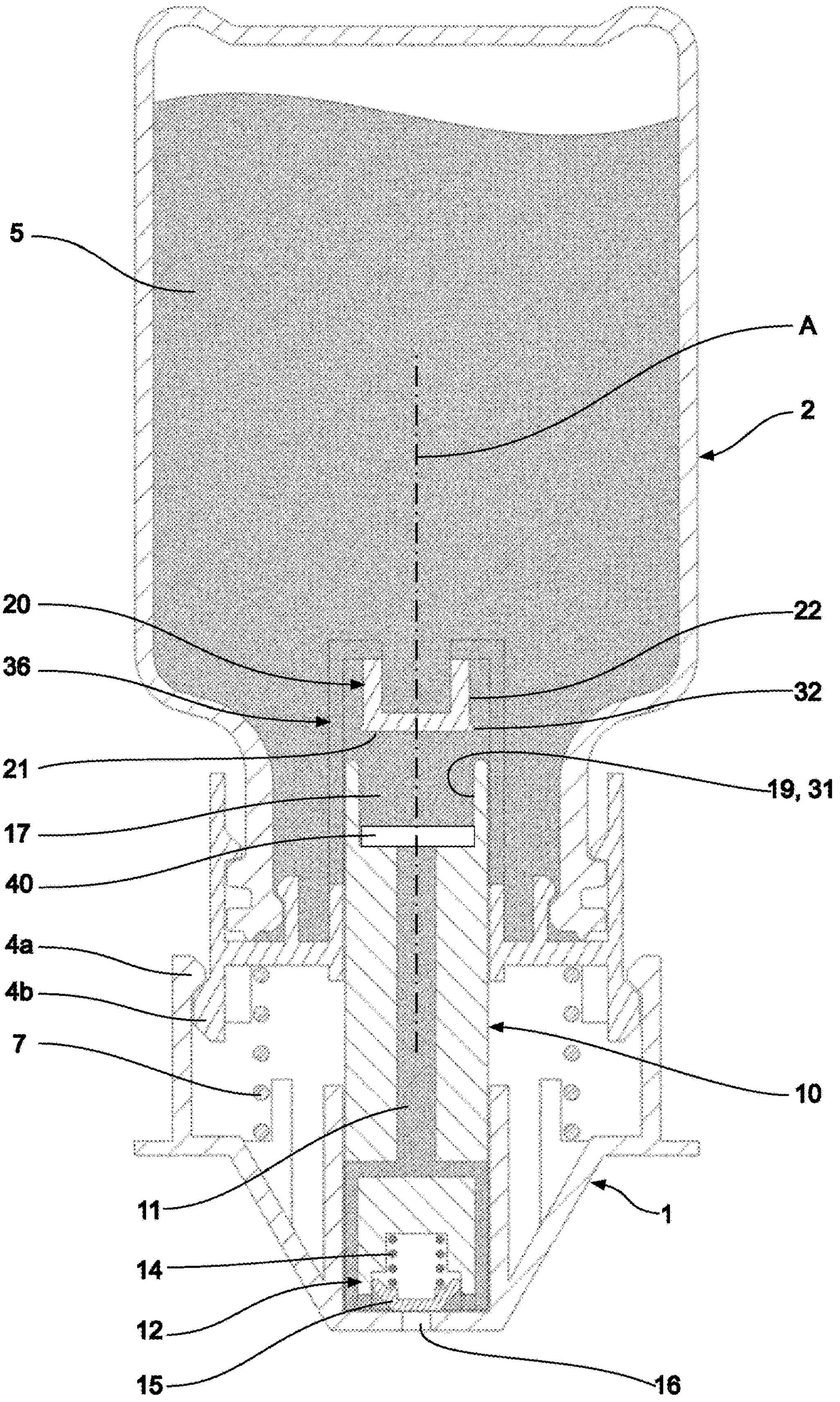
FIG. 1 shows a first embodiment of the device for the portioned dispensing of a liquid medium, namely in the still unactuated rest position or initial position.
Figure 2:
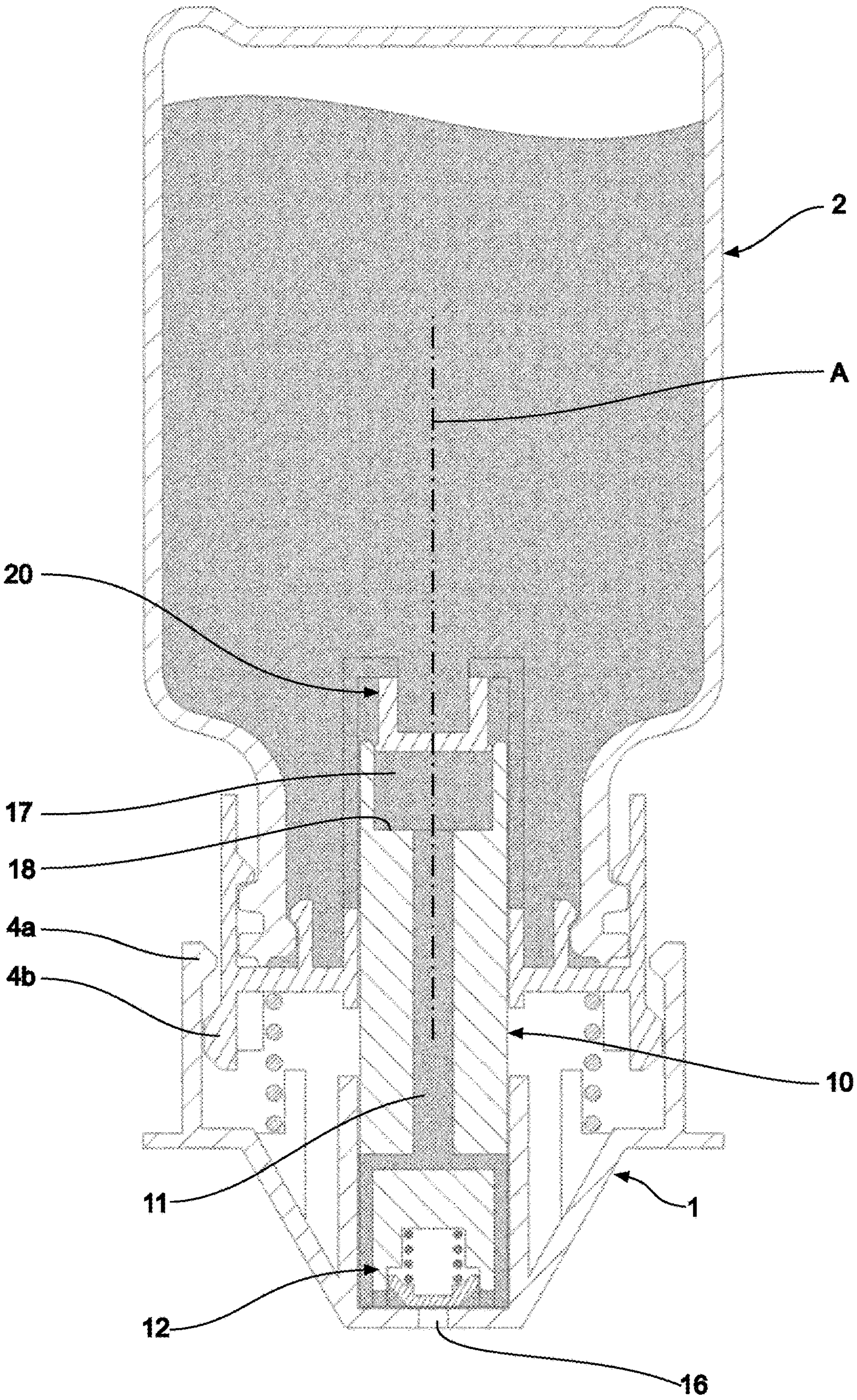
FIG. 2 shows the same device in an intermediate phase of operation, in which the dosing cavity is separated from the storage space for the first time.
Figure 3:
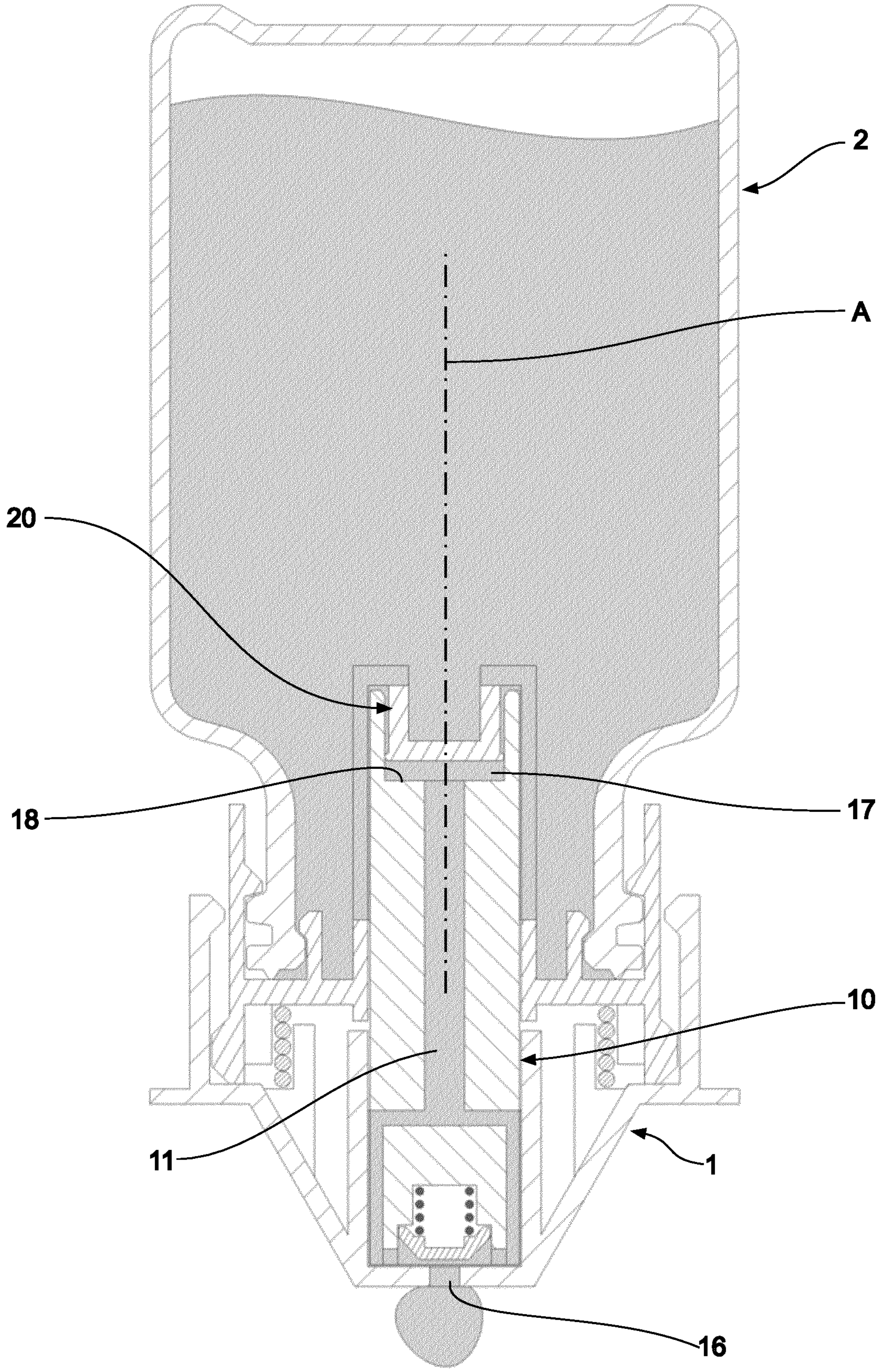
FIG. 3 shows the same device in the end position of actuation, i.e. at the end of the dispensing phase.

The device shown in FIGS. 1 to 3 in a first embodiment is used for the portioned dispensing of a liquid medium and specifically a therapeutic liquid, for example nasal drops or eye drops. The device can also be used to dispense other media and media for other purposes in portions, i.e. in defined and reproducible volume units. The device comprises a first housing part 1 and a second housing part 2, which are arranged to move longitudinally in relation to each other along a common longitudinal axis A between an unactuated rest position (FIG. 1) and an actuated end position (FIG. 3). Actuation by the user is usually carried out by hand, with the thumb pressing against the end of the second housing part 2 and two fingers simultaneously resting on the first housing part 1 and absorbing the counter-pressure.

The housing parts 1, 2 can be designed to be rotationally symmetrical, which facilitates handling. They are provided with locking structures 4*a*, 4*b* that operate on one side. Although these allow the two housing parts 1, 2 to be pushed together while dispensing, i.e. discharging a dosed quantity of liquid, they do not allow the two housing parts 1, 2 to be released from each other. A spring 7 between the housing parts 1, 2 ensures that they are pushed back into the initial or rest position when not actuated, i.e. until the locking structures 4*a*, 4*b* come into contact with each other.

Part of the second housing part 2 is a storage space 5, in which the liquid medium to be dispensed is stored. The quantity is sufficient to carry out a large number of discharges. Depending on the design of the housing parts 1, 2, the storage space 5 can also include parts of the space that are located inside the first housing part 1.

A piston 10 is part of the first housing part 1 and is therefore axially fixed to the first housing part. The piston 10 has the shape of a punch and extends along the longitudinal axis A. It is provided in its center with a liquid channel 11, which leads to a valve unit 12 arranged in the first housing part 1. In the drawings, the channel cross-section of the liquid channel 11 is exaggerated for reasons of representation.

Part of the valve unit 12 is a valve body 15, which is loaded in the closing direction by a closing spring 14 and operates in a pressure-dependent manner. In its closed position, as shown in FIG. 1, the valve body 15 closes a discharge opening 16, which is located at the end of the first housing part 1.

The valve body 15 is designed to open against the spring pressure of the closing spring 14 only when the pressure of the liquid medium is sufficiently high, thus releasing the discharge opening 16. In this way, liquid passes from the liquid channel 11, preferably with partial flow around the valve unit 12, to the discharge opening 16 and sprays out of it.

At its other end, the liquid channel 11 ends in a dosing cavity 17. The dosing cavity 17 is a pot-shaped, essentially cylindrical space at the end of the piston 10 and on the longitudinal axis A. The dosing cavity 17 is circumferentially enclosed by an inner wall 19 of the piston 10. The inner wall 19 is completely closed. At its one axial end, the dosing cavity 17 has a base 18 (FIG. 2), from which the liquid channel 11 extends. At its other end, the dosing cavity 17 is open.

A plunger 20 is part of the second housing part 2 and is therefore axially fixed to the second housing part. The plunger 20 also extends along the longitudinal axis A, and therefore in longitudinal alignment with the piston 10. The plunger 20 also has the shape of a punch and is composed of an end face 21, which faces the dosing cavity 17, and a plunger casing 22. The end face 21 is designed as a closed pressure surface. In the exemplary embodiment shown, the plunger casing 22 is also closed, but can also be provided with openings.

The plunger 20 of the second housing part 2, in cooperation with the piston 10 of the first housing part 1, is intended to be lowered into the dosing cavity 17 by and during actuation of the device, and in doing so to first portion a certain quantity of liquid in the dosing cavity and then to apply the pressure required to discharge the quantity of liquid. The relative movement carried out here takes place along the longitudinal axis A.

A phased seal between the dosing cavity 17 and the plunger 20 is required for both of these effects. For this purpose, the inner wall 19 of the piston 10 surrounding the dosing cavity 17 forms an inner sealing section 31. When the plunger 20 is at least partially lowered into the dosing cavity 17 (FIG. 2) and also when the plunger 20 is completely lowered into the dosing cavity 17 (FIG. 3), an opposite sealing section 32, which is located on the outside of the plunger casing 22, lies against the inner sealing section 31 without a gap. In the exemplary embodiment, this outer sealing section 32 is a sealing bead which runs in a ring around the plunger casing 22 at the level of the end face 22.

FIG. 2 shows the state of the initial contact between the piston 10 and the plunger 20, wherein this contact takes place at the sealing sections 31, 32. From this point 35 onwards, portioning in the dosing cavity 17 is complete. No more liquid can enter the dosing cavity. From this point on, the pressure phase begins with discharge of the dispensed quantity of liquid. Its completion is shown in FIG. 3.

In contrast, FIG. 1 shows for the not yet actuated rest or initial state that in this state there is still no seal between the inner wall 19 of the piston 10 and the plunger 20, since in this state the piston 10 is still arranged at an axial distance from the plunger 20, therefore the sealing sections 31, 32 are also not yet in contact, and therefore therapeutic fluid can enter the dosing cavity 17 unhindered. In particular, the arrangement of the inner and outer sealing sections 31, 32 is therefore located in the storage space 5 and is surrounded by the storage space 5, which leads to a reliable inflow of liquid from the storage space into the dosing cavity 17.

The fact that the plunger 20 is arranged on a plunger carrier 36, which is located in the storage space 5 and is provided with several openings 37 through which the medium can flow, also contributes to this inflow. The openings 37 are arranged distributed over the circumference of the plunger carrier 36, preferably evenly distributed. The interior of the plunger carrier 36 forms a movement space for the piston 10, which moves axially therein.

In order to keep the mechanical stress in the edge areas low in the intermediate phase shown in FIG. 2, in which the sealing sections 31, 32 come into contact for the first time, the inner wall 19 of the dosing cavity 17 is designed as a circular cylindrical longitudinal section over the majority of its length, which is adjoined by a shorter, conically tapering longitudinal section towards the plunger 20.

FIG. 1 also shows a valve 40, which is arranged between the dosing cavity 17 and the liquid channel 11 and, in the exemplary embodiment, is positioned at the base 18 of the cavity 17. The valve 40 is not explicitly shown in the other figures in the drawing. The valve 40 enables compression in the dosing cavity 17 during the displacement phase. It only opens when the discharge phase is reached and then releases the liquid channel 11 for the dosed quantity of liquid to flow through. After completion of the liquid discharge, the valve 40 prevents backflow or contamination of the residual volume in the piston bore. The dosing device can therefore constructively and functionally protect the filling material in the container against contamination.

Figure 4:
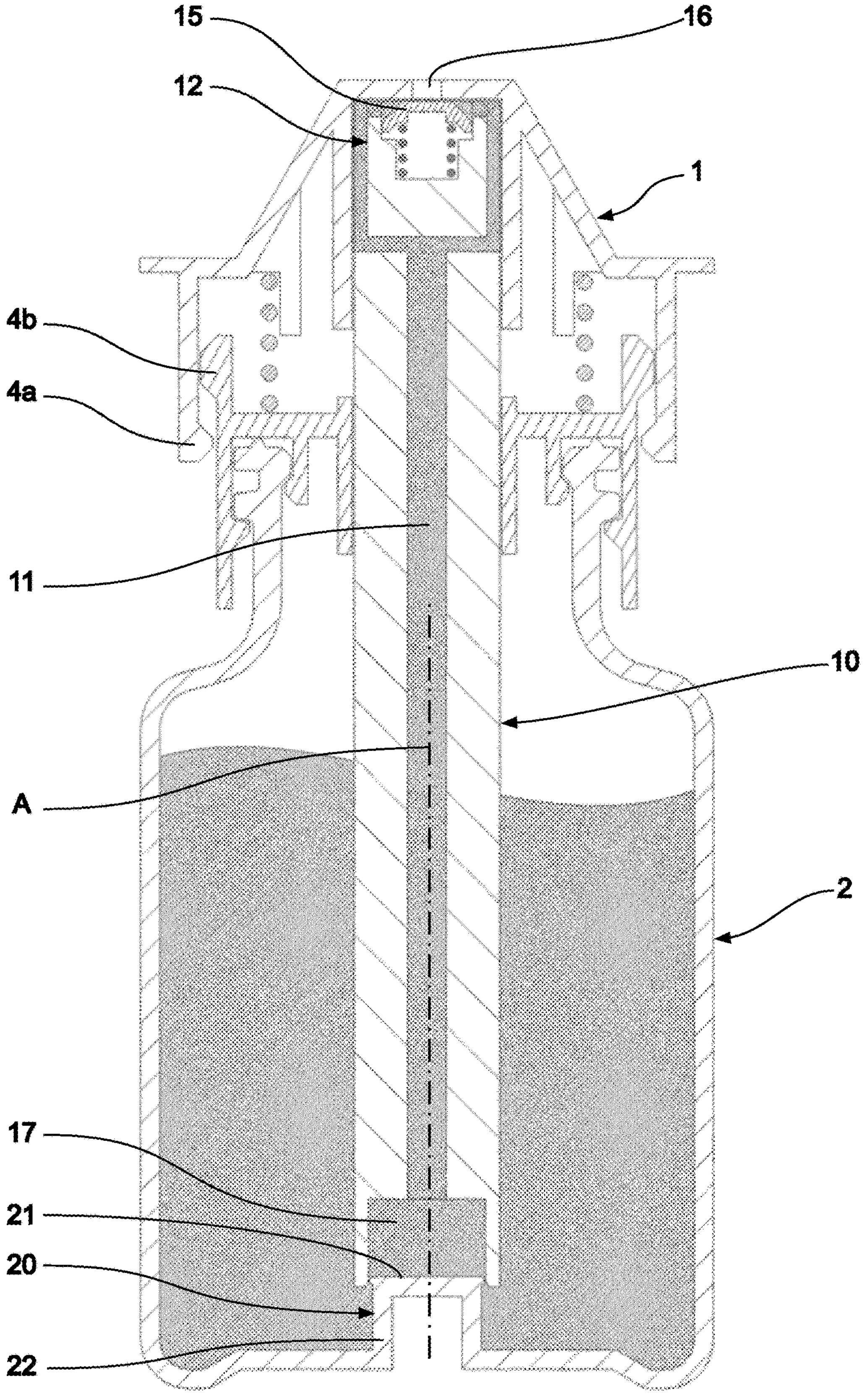
FIG. 4 shows a second embodiment of the device for the portioned dispensing of a liquid medium, namely in the intermediate phase, as shown in FIG. 2 for the first embodiment.

FIG. 4 shows a second embodiment of the device. Only the intermediate phase is shown, as shown in FIG. 2 for the first embodiment. When handling the second embodiment, the arrangement of the housing parts is the reverse of that shown in FIGS. 1 to 3. The first housing part 1 with the piston 10 and the discharge opening 16 is located at the top, and the second housing part 2 with the plunger 20 is located at the bottom. Due to the upwardly directed discharge opening 16, this embodiment is suitable for administering nasal drops, for example, whereas the first embodiment is more suitable for administering eye drops in the field of medicine.

Figure 5:
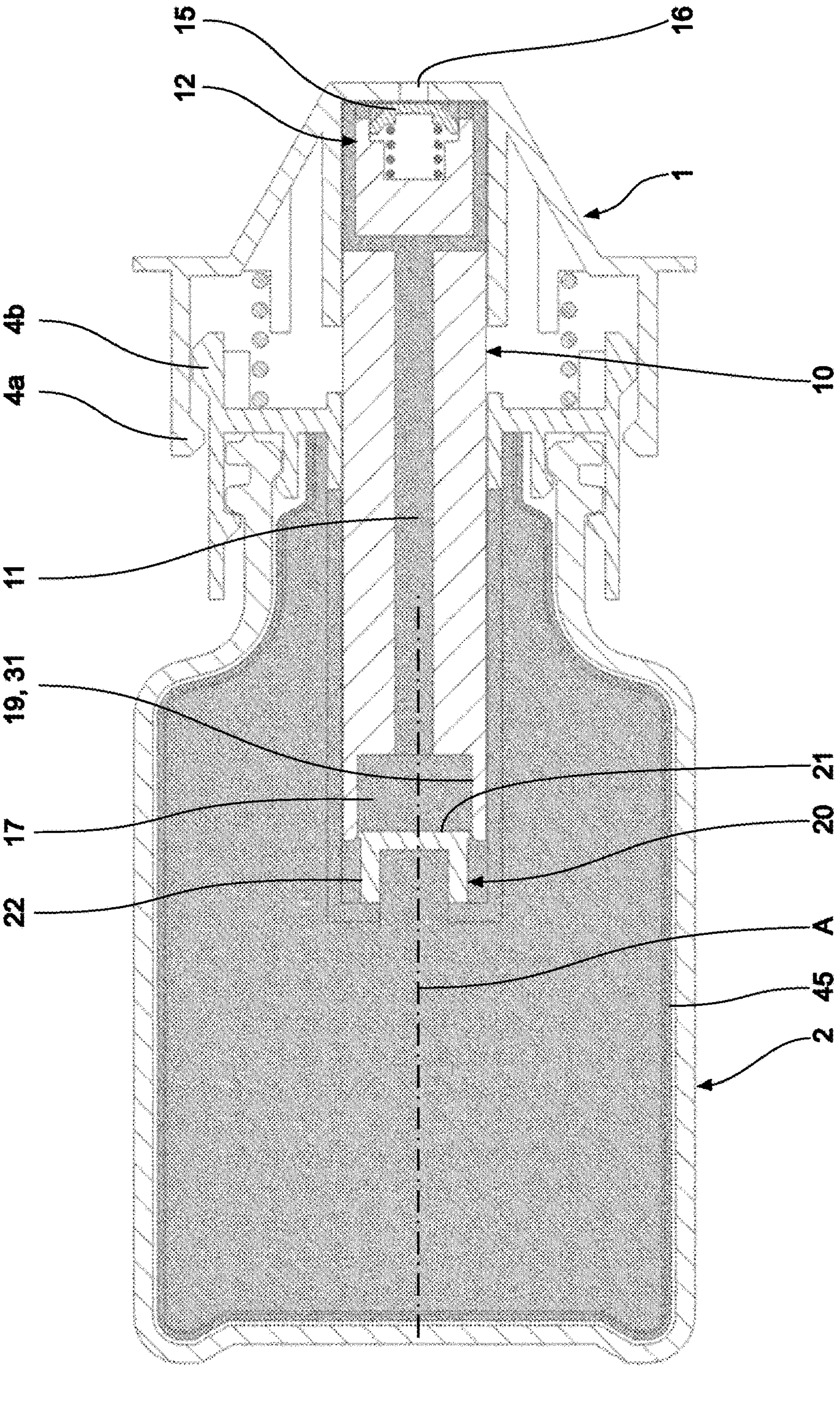
FIG. 5 shows a third embodiment of the device for the portioned dispensing of a liquid medium, again in the intermediate phase, as shown in FIG. 2 for the first embodiment.

FIG. 5 shows a third embodiment. Again, only the intermediate phase is shown, as shown in FIG. 2 for the first embodiment and in FIG. 4 for the second embodiment.

When handling the third embodiment, the arrangement of the housing parts 1, 2 is of no great significance. As an example, the arrangement with a horizontal longitudinal axis A is shown here, so that the discharge opening 16 is also horizontal for a corresponding application.

In FIG. 5, the storage space 5 for the liquid medium to be dispensed is again enclosed by the solid housing material of the second housing part 2, and additionally by an inner lining 45 in the form of a bag. The lining 45 is made of flexible material that is impermeable to liquid. It initially lies against the inner wall of the housing part 2, but is not connected to it and is also designed and sealed in such a way that the stored liquid is completely enclosed in an airtight manner. If the volume of liquid gradually decreases as a result of repeated discharge, this leads to a corresponding reduction in the size of the lining 45 as the bag contracts. However, the (residual) storage space 5 enclosed in this way always remains completely filled with liquid medium, and thus also the area around the dosing cavity 17.

The invention claimed is:

1. A device for the portioned dispensing of a liquid medium, the device comprising: first and second housing parts which are arranged to be longitudinally movable relative to one another on a common longitudinal axis (A) between an unactuated rest position and an actuated end position, a piston arranged axially fixed to the first housing part, a plunger arranged axially fixed to the second housing part, which is arranged in longitudinal alignment with the piston and is composed of a closed end face and a plunger casing, a dosing cavity which is enclosed by an inner wall of the piston and into which the plunger is configured to be lowered by actuation of the device, and a liquid channel which extends from the dosing cavity and is in fluid communication with a valve-controlled discharge opening in the first housing part, wherein the liquid channel extends inside the piston from the base of the dosing cavity to the valve-controlled discharge opening, wherein an inner sealing section formed on the inner wall of the piston, against which an outer sealing section formed on the outside of the plunger casing rests without a gap when the plunger is partially and fully lowered into the dosing cavity, wherein the actuation of the device is divided into individual phases, a first phase being the still unactuated rest or initial state, in which there is no contact and therefore no mutual sealing between the piston and the plunger, therapeutic fluid being able to flow unhindered from a fluid supply in a storage space surrounding the dosing cavity into the dosing cavity and fill the dosing cavity in the first phase, in a second and third phase, with the plunger partially lowered into the dosing cavity and with the plunger fully lowered, the inner sealing section rests against the opposite outer sealing section without any gaps, so that the dosing cavity is separated from the fluid supply of the surrounding storage space from the second phase onwards and, in the third phase, pressure is applied to the medium thus separated, causing the medium to be pressed toward the discharge opening and to leave the discharge opening.

2. The device according to claim 1, wherein the valve-controlled discharge opening is located on the first housing part.

3. The device according to claim 1, wherein part of the second housing part is a storage space storing the medium.

4. The device according to claim 3, wherein the arrangement of the inner and outer sealing sections is located in the storage space and is surrounded by the storage space.

5. The device according to claim 3, wherein the plunger is arranged on a plunger carrier facing away from the end face, and in that the plunger carrier is located in the storage space and is provided with a plurality of openings through which the medium is configured to flow.

6. The device according to claim 5, wherein the openings are arranged distributed around the circumference of the plunger carrier.

7. The device according to claim 5, wherein the interior of the plunger carrier is designed as a movement space for the piston arranged axially movably therein.

8. The device according to claim 1, wherein the inner wall of the dosing cavity is designed over the predominant part of a length of the dosing cavity as a circular cylindrical longitudinal section which is adjoined by a conically tapering longitudinal section towards the plunger.

9. The device according to claim 1, whereby a valve arranged in the transition between the dosing cavity and the liquid channel.

10. The device according to claim 9, wherein the valve enables compression in the dosing cavity in a displacement phase and only opens when a discharge phase is reached and releases the liquid channel for the medium to flow through, and in that the valve prevents leakage, backflow or contamination of the medium stored in the storage space after the discharge has been completed.

* * * * *